United States Patent [19]

Williamson

[11] 4,246,281
[45] Jan. 20, 1981

[54] PHARMACOLOGICALLY ACTIVE ACENAPHTHENE DERIVATIVES

[75] Inventor: William R. N. Williamson, Slough, England

[73] Assignee: Lilly Industries Limited, London, United Kingdom

[21] Appl. No.: 74,220

[22] Filed: Sep. 10, 1979

[51] Int. Cl.³ .................. C07C 69/616; A61K 31/235; A61K 31/19; C07C 57/40
[52] U.S. Cl. ............................ 424/308; 560/100; 560/8; 562/405; 562/490
[58] Field of Search ............... 562/405, 490; 560/100, 560/8; 424/308, 317

[56] References Cited

U.S. PATENT DOCUMENTS

| 3,274,240 | 9/1966 | Fritz | 562/405 |
| 3,452,085 | 6/1969 | Lauria | 562/405 |
| 3,732,299 | 5/1973 | Levine | 562/405 |

Primary Examiner—Natalie Trousof
Assistant Examiner—Michael Shippen
Attorney, Agent, or Firm—James L. Rowe; Arthur E. Whale

[57] ABSTRACT

Acenaphthenes of formula (I)

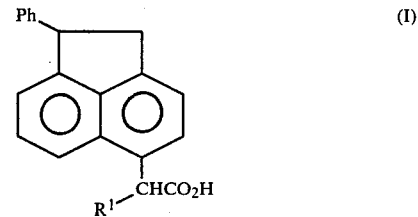

where Ph represents an optionally substituted phenyl group and wherein $R^1$ represents hydrogen or $C_{1-4}$ alkyl are useful anti-inflammatory agents.

5 Claims, No Drawings

PHARMACOLOGICALLY ACTIVE ACENAPHTHENE DERIVATIVES

This invention relates to certain novel acenaphthene derivatives which have been found to possess useful pharmacological activity, to the use of such derivatives as pharmaceuticals, especially as anti-inflammatories and to pharmaceutical formulations containing the new acenaphthene derivatives as an active ingredient.

According to the present invention therefore there is provided a novel acenaphthene derivative of formula (I):

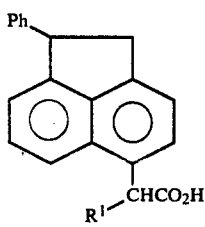

where Ph represents phenyl optionally substituted by halogen and $R^1$ represents hydrogen or $C_{1-4}$ alkyl; or a pharmaceutically acceptable salt or $C_{1-4}$ alkyl ester thereof.

When $R^1$ is $C_{1-4}$ alkyl it is preferably methyl. The preferred halogen is chlorine. Ph preferably signifies unsubstituted phenyl.

The acenaphthenes of the invention can be prepared from the known starting material 3-phenyl-1-indanone by utilising the following reaction sequence:

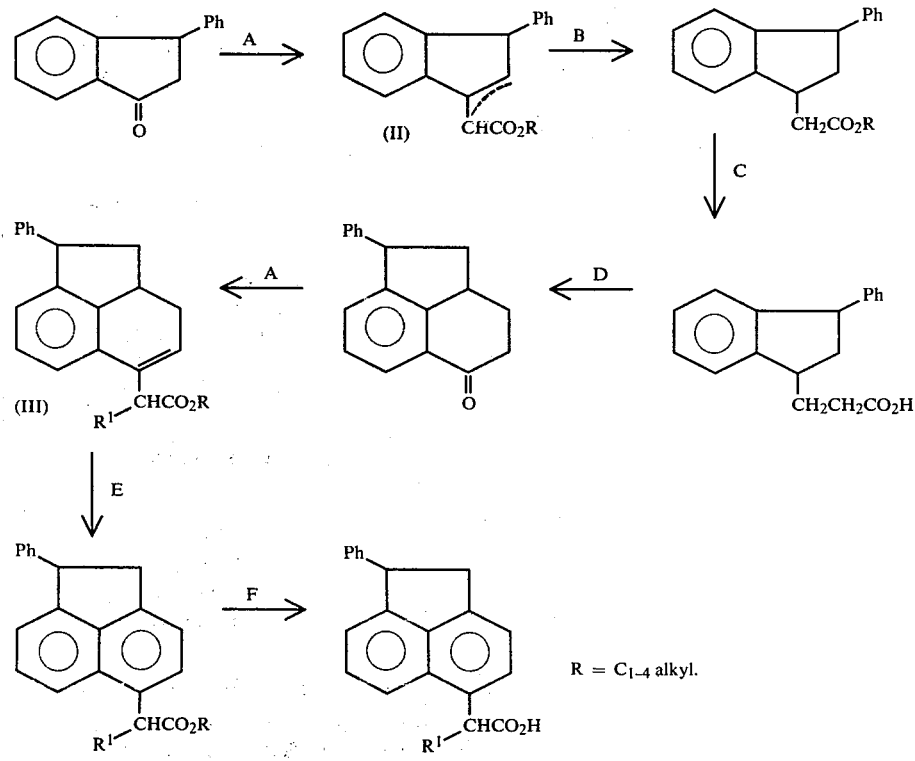

$R = C_{1-4}$ alkyl.

Reaction A is, of course, the well-known Reformatskii reaction as described in for example *Organic Reactions* 1, 1, (1942). The product of the reaction is a mixture of the endo and exocyclic olefinic esters as indicated by the dotted line in the formula II structure.

The reduction B can be effected by catalytic hydrogenation using for example palladium on charcoal.

Reaction C involves the addition of one methylene group to the side chain and can be accomplished by any method well-known to those skilled in the art, for example, by reducing the ethyl ester to the corresponding alcohol with $LiAlH_4$ in tetrahydrofuran, converting the alcohol thus formed to the corresponding bromo compound with HBr, reacting this bromo compound with NaCN and then hydrolysing the nitrile thus formed with a mineral acid such as hydrochloric acid.

The internal Friedel-Crafts reaction D can be effected by forming the acid chloride with $PCl_5$ using as catalyst aluminium chloride and benzene as solvent.

The aromatisation reaction E can be effected by stirring the ester III with palladium and charcoal at a temperature of approximately 200° C.

Finally, the hydrolysis F can be effected using any suitable hydrolytic method although it is preferred to employ alkaline hydrolysis utilising, for example, caustic soda in ethanol.

Salt forms of the compounds of formula I can be obtained in conventional manner and as examples of pharmaceutically-acceptable salt forms may be given the alkali-metal and alkaline earth metal salt forms such as the sodium, calcium and magnesium salt forms.

The acenaphthenes of formula I, and their pharmaceutically-acceptable salts and esters, are useful in that they possess pharmacological activity. In particular, they have been shown to have low toxicity and to possess analgesic, antipyretic and/or anti-inflammatory activity, particularly anti-inflammatory activity as indicated in the well-known Carrageenan and the rat adjuvant arthritis test. They are particularly indicated for use in the treatment of rheumatoid arthritis.

The foregoing activities have been demonstrated in tests carried out in animals usually at doses of from 0.1 to 250 mg./kg. In the treatment of humans, the dose administered may be, for example, between 1 and 25 mg./kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 10 to 1000 mg. (preferably 25 to 500 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicylic acid and salts thereof, caffeine, codeine phosphate, phenylbutazone, paracetamol, dextropropoxyphene and indomethacin.

The compositions of the present invention will of course be adapted to the particular route of administration. Thus, for oral administration, tablets, pills, capsules, solutions or suspensions may be used; for parenteral administration, suppositories may be used; and for topical administration, creams, lotions or ointments may be used. Any of the foregoing compositions may, of course, be formulated in delayed or sustained release form in a manner well known in the art.

The compounds of formula I possess a chiral centre at the carbon atom of the acenaphthene nucleus to which the group Ph is attached, a further chiral centre arising when $R^1$ is other than hydrogen. Accordingly, the compounds can exist in optically active enantiomeric, dl and racemate form and, when $R^1$ is other than hydrogen, in diastereoisomeric form. The present invention is not intended to be limited to any particular form.

The following examples will further illustrate the invention:

EXAMPLE 1

3-Phenyl-1-indanacetic acid

3-Phenyl-1-indanone (83 g, 0.4 mol) was dried by refluxing in $C_6H_6$ (120 ml) with removal of the azeotroped $H_2O$. To this solution was added $Et_2O$ (120 ml) and Zn wool (26.25 g, 0.4 mol). The reaction mixture was heated to near reflux and a crystal of $I_2$ added. Ethyl bromoacetate (110 g, 0.6 mol) was added over 2 hours, the temperature being kept near reflux by heat of reaction and some external heating. After the addition, the mixture was stirred and refluxed for a further 0.5 hour, cooled and poured into ice and acetic acid. The mixture was extracted with $Et_2O$. The $Et_2O$ was washed with 1% $NH_4OH$, dried ($Na_2SO_4$), filtered and evaporated and the residue distilled to give a mixture of ethyl 3-phenylindene-1-acetate and its corresponding double bond isomer (83.6g) b.p. 145°–155° C. (0.1 mm). This mixture of esters was hydrogenated over 10% Pd/C (0.6g) to give ethyl 3-phenylindan-1-acetate. This ester was hydrolyzed by refluxing with sodium hydroxide in ethanol to give the title compound, m.p. 126°–9° C.

EXAMPLE 2

3-(3-Phenyl-1-indan)propionic acid

Ethyl 3-phenylindan-1-acetate (84.3 g, 0.3 mol) in THF (300 ml) was added dropwise with stirring to $LiAlH_4$ (10 g) in THF (200 ml) under $N_2$ and the mixture stirred at 80° C. overnight. Processing by standard conditions yielded 2-(3-phenylindan-1-yl)ethanol as an oil (47.3 g), IR 3100–3600 $cm^{-1}$ (OH). This alcohol could also obtained by reduction of the ester in THF using $LiBH_4$. The alcohol (43.15 g, 0.18 mol) was refluxed overnight with 48% HBr (280 ml), cooled, extracted with ether which, with standard processing, gave 2-(3-phenylindan-1-yl) ethyl bromide (50.8 g) as an oil. This bromo-compound (41.8 g, 0.14 mol) in $Me_2CO$ (160 ml) was added to a solution of NaCN (7 g, 0.143 mol) in $H_2O$ (40 ml) and the solution stirred and refluxed for 64 hours. The solution was evaporated to dryness and the product extracted with a mixture of AcOEt and $H_2O$. After drying ($Na_2SO_4$), filtration and evaporation 3-(3-phenylindan-1-yl)propionitrile (26.8 g) was obtained as a solid, IR 2250 $cm^{-1}$ (CN). This nitrile (24.3 g, 0.1 mol) in hot $EtOCH_2CH_2OH$ (100 ml) was treated with NaOH (24.3 g, 0.6 mol) in $H_2O$ (40 ml) and the solution refluxed for 6 hours. It was then poured into conc. HCl (50 ml) in $H_2O$ (250 ml), extracted with $Et_2O$ and the $Et_2O$ extracted with 2N NaOH. Acidification gave the title compound. NMR ($CCl_4$)δ1.5–3.3 (7H, $CH_2$), 4.12 (1H, CH), 6.8–7.3 (9H,Ar), 11.92 (1H, exchangeable). cl EXAMPLE 3

1-Phenyl-2a,3,4,5-tetrahydro-5-acenaphthenone 3-(3-Phenyl-1-indan)propionic acid (32 g, 0.12 mol) was dried by refluxing in $C_6H_6$ (200 ml) with removal of azeotroped $H_2O$. The solution was added to a stirred suspension of $PCl_5$ (29 g, 0.14 mol) in $C_6H_6$ (50 ml) and stirred for 1.5 hours. The solution was then added to a cooled, stirred suspension of $AlCl_3$(29 g) in $C_6H_6$ and stirring continued at room temperature for 3 hours. The mixture was poured into ice and HCl and extracted with Et$_2$O. The Et$_2$O was washed (NaHCO$_3$ solution), dried (Na$_2$SO$_4$) and evaporated to give the title compound (25.7 g), m.p. 99° C. (MeOH).

EXAMPLE 4

Ethyl 1-phenyl-5-acenaphthenyl aetate

Ethyl 1-phenyl-2a,3-dihydro-5-acenaphthenyl acetate (18.3g, 0.058 mol) was stirred with 10% Pd/C (1.8 g) under N$_2$ at 200°–210° C. for 2hours. The cooled product dissolved in CHCl$_3$ was filtered and evaporated to give the title product as an oil (17.9 g).

EXAMPLE 5

1-Phenyl-5-acenaphtheneacetic acid

The ester of Example 4 was hydrolysed to the title compound, m.p. 200° C., with caustic soda in ethanol.

EXAMPLE 6

Similarly, using the procedures of Examples 1 to 5 there was prepared: α-Methyl-1-phenyl-5-acenaphtheneacetic acid; m.p. 199° C.

I claim:

1. An acenaphthene derivative of formula (I):

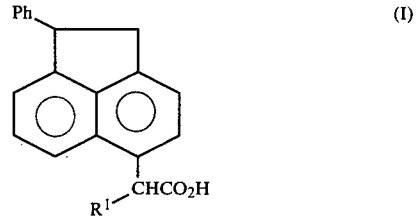

wherein Ph represents phenyl optionally substituted by halogen and $R^1$ represents hydrogen or $C_{1-4}$ alkyl; or a pharmaceutically-acceptable salt or $C_{1-4}$ alkyl ester thereof.

2. A compound of claim 1, being:
1-Phenyl-5-acenaphtheneacetic acid.

3. A compound of claim 1, being:
Ethyl 1-phenyl-5-acenaphthenyl acetate.

4. A compound of claim 1, being:
α-Methyl-1-phenyl-5-acenaphtheneacetic acid.

5. A pharmaceutical composition comprising, as an active ingredient, an anti-inflammatorily effective amount of a compound of claim 1 associated with at least one pharmaceutically-acceptable carrier.

UNITED STATES PATENT AND TRADEMARK OFFICE
CERTIFICATE OF CORRECTION

PATENT NO. : 4,246,281

DATED : January 20, 1981

INVENTOR(S) : William R. N. Williamson

It is certified that error appears in the above-identified patent and that said Letters Patent are hereby corrected as shown below:

The following should be added to the cover page:

--[30] Foreign Application Priority Date
September 16, 1978 [GB] United Kingdom
37122/78.--

Signed and Sealed this

Second Day of June 1981

[SEAL]

Attest:

RENE D. TEGTMEYER

Attesting Officer

Acting Commissioner of Patents and Trademarks